United States Patent [19]
Arcusin

[11] Patent Number: 5,135,495
[45] Date of Patent: Aug. 4, 1992

[54] SELF DISCARDING SYRINGE

[76] Inventor: Carlos E. Arcusin, Lavalle 1977, piso 1°, of. "C" 1051, Buenos Aires, Argentina

[21] Appl. No.: 497,501

[22] Filed: Mar. 22, 1990

[30] Foreign Application Priority Data

Mar. 22, 1989 [AR] Argentina ............................... 313481

[51] Int. Cl.⁵ ............................................. A61M 5/50
[52] U.S. Cl. ..................................... 604/110; 604/220; 604/228
[58] Field of Search ............... 604/110, 195, 196, 208, 604/210, 218, 228, 220, 221, 229

[56] References Cited
U.S. PATENT DOCUMENTS

| | | | |
|---|---|---|---|
| 2,072,327 | 3/1937 | Friedman et al. ................... | 604/228 |
| 3,828,778 | 8/1974 | Weinhart ......................... | 604/228 X |
| 4,159,713 | 7/1979 | Prais ................................. | 604/228 X |
| 4,391,272 | 7/1983 | Staempfli ........................ | 604/110 |
| 4,863,427 | 9/1989 | Cocchi ............................ | 604/110 |
| 4,915,692 | 4/1990 | Verlier .............................. | 604/110 |
| 4,986,813 | 1/1991 | Blake, III et al. .................. | 604/110 |
| 5,078,686 | 1/1992 | Bates ................................ | 604/110 |

Primary Examiner—John D. Yasko
Assistant Examiner—Adam J. Cermak
Attorney, Agent, or Firm—Michael J. Striker

[57] ABSTRACT

A self-discarding syringe has a tube having a spout at an end thereof, and a piston including two elements movable relative to each other. One of the two elements is rigid and another of the two elements is resilient. The tube has a limitation for limiting displacement of the piston means away from the spout.

9 Claims, 3 Drawing Sheets

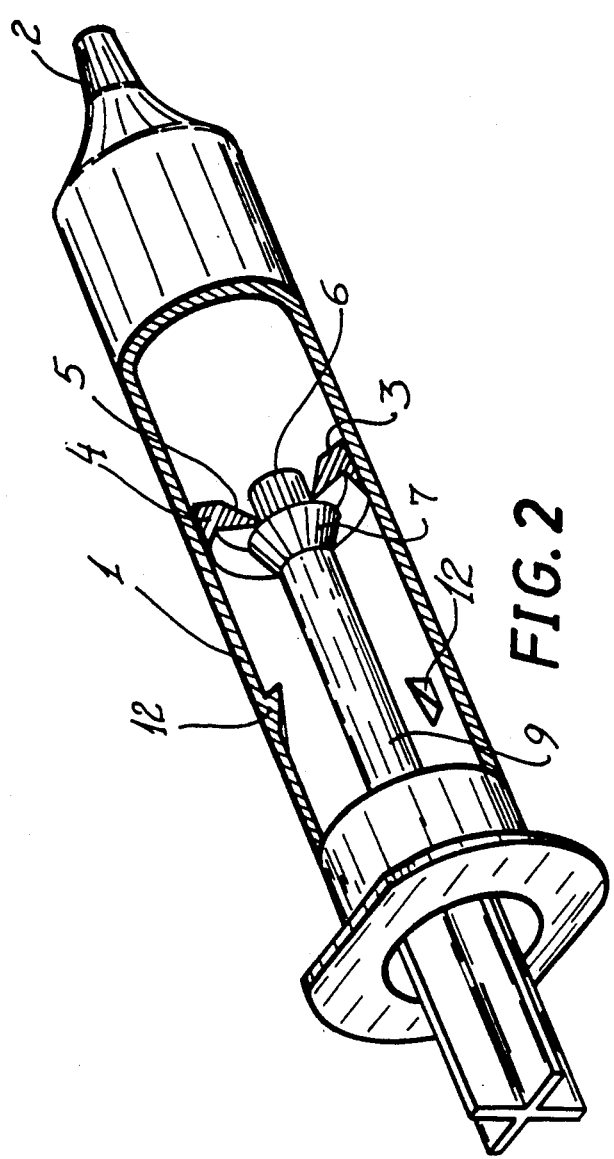
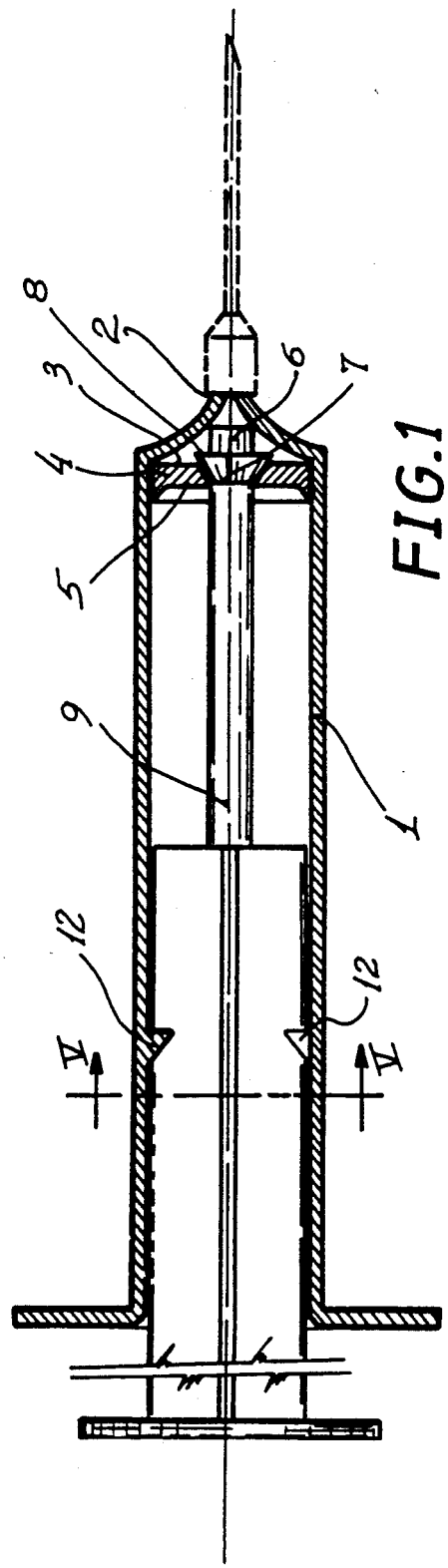
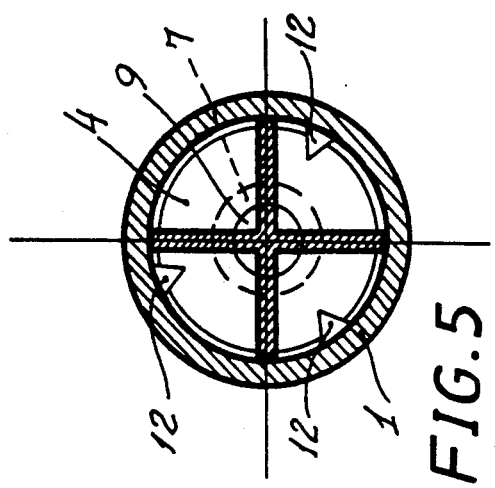

SELF DISCARDING SYRINGE

BACKGROUND OF THE INVENTION

The present invention relates to a self-discarding syringe to be used in medical field, as well as in other fields where it is necessary to use it only once.

It is known to utilize syringes which can be used only once in medical fields, in view of danger of contamination and to prevent tricks allowing repeated use of the same.

Known syringes are still repeatedly used although they were designed as disposable elements and therefore must be used only once. Their reuse is not prevented and therefore the patient is not sure that this element was not used before.

SUMMARY OF THE INVENTION

It is an object of the present invention to provide a self-discarding syringe which can be used only once.

This object of the invention is achieved with a syringe in which one loading operation can be performed with injection means, and only one injection operation with ejection means, because the mechanism which forms a piston and a stem controlling it, together with piston displacement limitation means provided in a syringe body, determine that the piston after its opposite strokes inside the syringe body will stay inoperable notwithstanding the stem displacement or the intention to bind the stem with the piston through external actions.

In order to remain inoperable, the new syringe has a piston formed by two independent and complementary bodies. One of the bodies frictionally engages the internal walls of the syringe during its displacement, while the other of the bodies is an element having a predetermined geometrical configuration and connected to the stem, so as to allow modification of its position with respect to the first body when it crosses a hole provided in the middle of the first body. Therefore the first body may be drawn in one direction and pushed only once in the opposite direction. This is possible because one of the bodies is flexible and the other of the bodies is rigid, and means is provided to limit the displacement of the piston inside the syringe.

The self-discarding syringe of the present invention is formed as a tube-shaped body with a spout at its end. The piston fits perfectly well in the cavity of the body and displaces in it. The piston is formed by the above-mentioned two complementary elements. The first element fits in the cavity of the syringe body, while the second element has a geometrical configuration selected from truncated conical, cylindrical, semi-cylindrical or polygonal affixed to a rod performing the piston displacement.

A second element may change its location with respect to the first element when it passes through a hole of the first element having a smaller diameter than the second element. This is so since one of the elements is made of flexible material and the other element is made of rigid material and the syringe body has in its part a displacement limiting means for the piston. This allows the second element to which the piston is coupled to change its position with respect to the first element.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 shows a cross-sectional view of a syringe according to the present invention;

FIG. 2 shows a partially cut perspective view of the syringe shown in FIG. 1;

FIG. 5 shows a cross-sectional view along the line V—V in FIG. 1 and showing limitation means of the inventive syringe;

DESCRIPTION OF THE PREFERRED EMBODIMENTS

Figure 3:
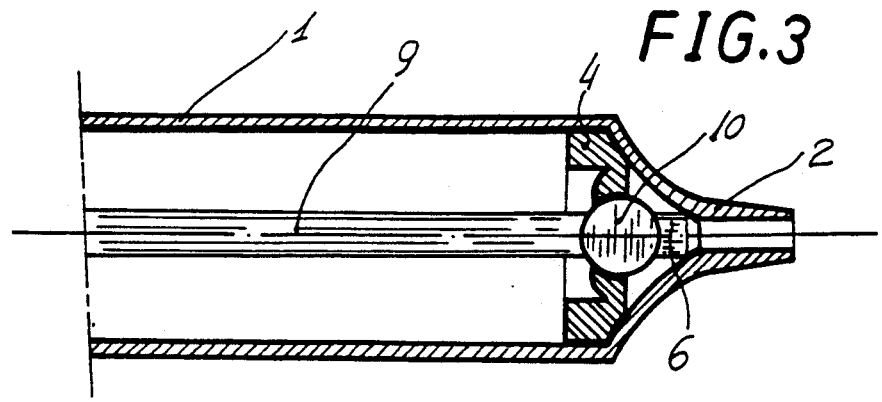
FIG. 3 shows one embodiment of the piston of the syringe according to the present invention.

A self-discarding syringe in accordance with the present invention includes a body 1 formed by a tube with a spout at its extreme end 2. A piston 3 is movable inside the body 1.

The piston 3 has a first ring-shaped element 4 with an external outline which is similar to the internal outline of the tube of the body 1. In its central part it has a hole 5 of a diameter slightly bigger than the diameter of guide-butt 6 provided in a second element 7 of the piston 3.

The second element 7 has the shape of a truncated cone 8 in the embodiment of FIG. 3. It smaller base is connected to the stem 9 which operates the piston 3. The bigger base of the truncated cone 8 is connected to the guide-butt 6. The truncated cone 8 is placed with its smaller conical part introduced in the hole 5 of the element 4 when the piston 3 is positioned at the end of the body 1 having the spout 2.

In another embodiment shown in FIG. 3 the second element has a spherical shape 10, and the guide-butt 6 and the stem 9 are fixed in diametrically opposite parts of the sphere.

Figure 4:
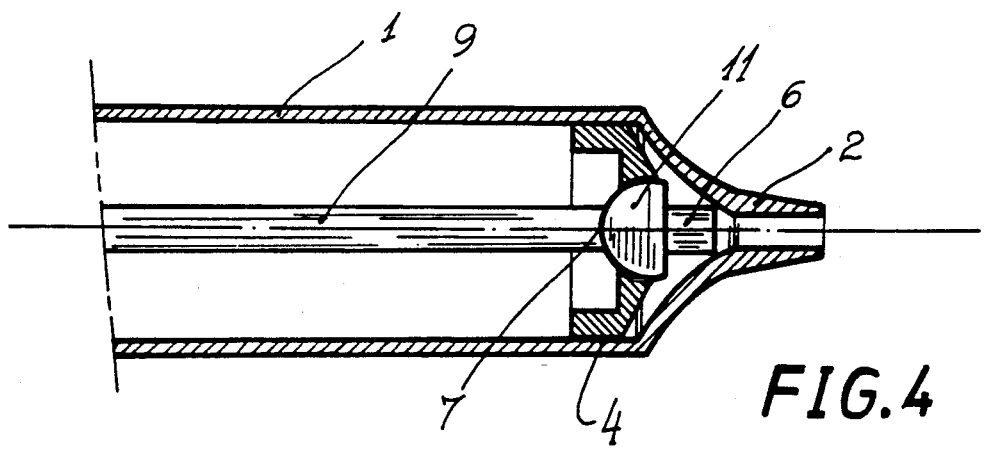
FIG. 4 shows another embodiment of the piston of the syringe according to the present invention.

Furthermore, as shown in FIG. 4, the second element 7 is formed by a semisphere 11 with the stem 9 attached to its spherical part and the guide-butt 6 attached to the flat part. The second element 7 may also have polygonal geometrical configurations forming a complementary element, to form the piston 3.

Figure 7:
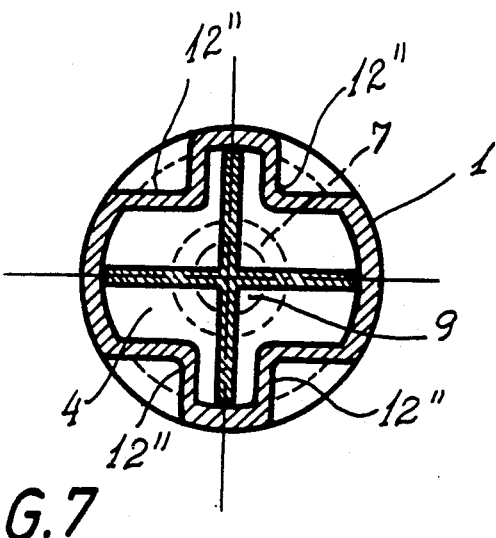
FIGS. 6 and 7 show cross-sectional views of another embodiment of the limitation means.
Figure 6:
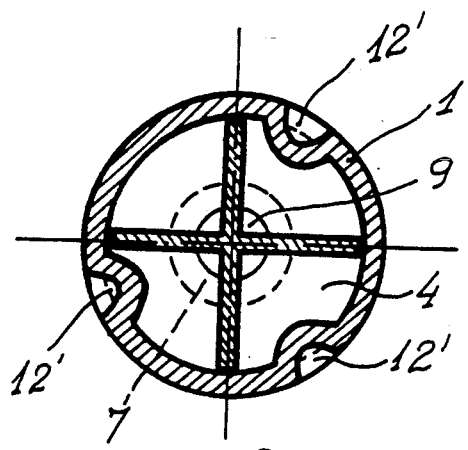

The body 1 of the syringe has limitation means 12 for limiting the displacement of the piston. The limitation means may be formed by projections arranged at 120° relative to one another as shown in FIG. 5. The limitation means can also be formed as deformation means of the tube body as shown in FIGS. 6 and 7. The stem 9 which operates the piston 3 may be cylindrical or may have another cross-section adequate for its use. The deformations of FIG. 6 are identified as 12' and formed by partially circular inwardly bent walls of the syringe body, while the deformations of FIG. 7 are identified as 12" and formed as right-angled inwardly bent walls of the syringe body.

FIGS. 8-12 illustrate the operation of the discarding syringe of the present invention.

Figure 8:
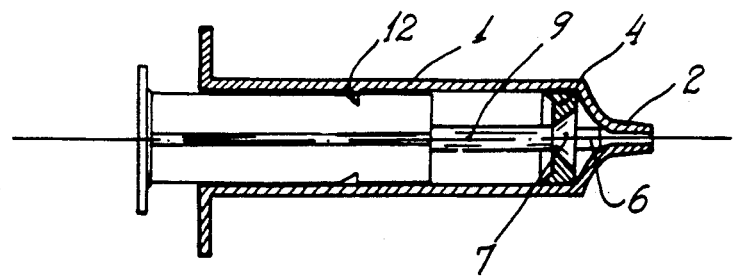
FIGS. 8, 9, 10, 11 and 12 show the positions of the piston and its forming element during a syringe operation.
Figure 9:
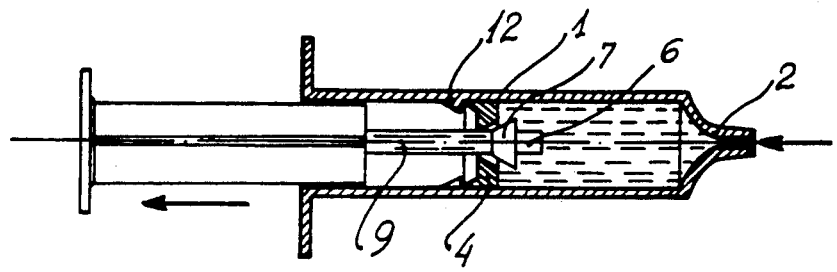

When the piston is placed near the spout 2 as shown in FIG. 8, which is a necessary condition to fill the syringe, the second element 7 is placed between the end of the body 1 and the first element 4. When the piston is then withdrawn by actuation of its stem to absorb the medium to be introduced into the syringe, the element 7 is introduced into the hole 5 of the body 4 forming a water-tight unit, as shown in FIG. 9.

Figure 10:
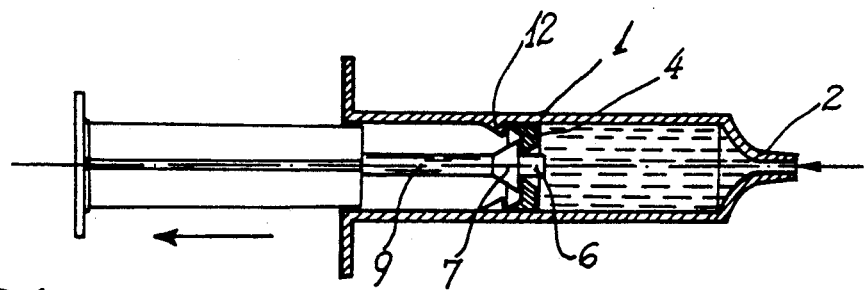

When the piston 3 reaches the displacement limitation means 12 and one wishes to eject the medium introduced into the syringe, the syringe stem must continue to be operated in the same direction until the second element 7 occupies the position shown in FIG. 10. This is because one of the elements 4 and 7 is elastic and the other is rigid.

Figure 11:
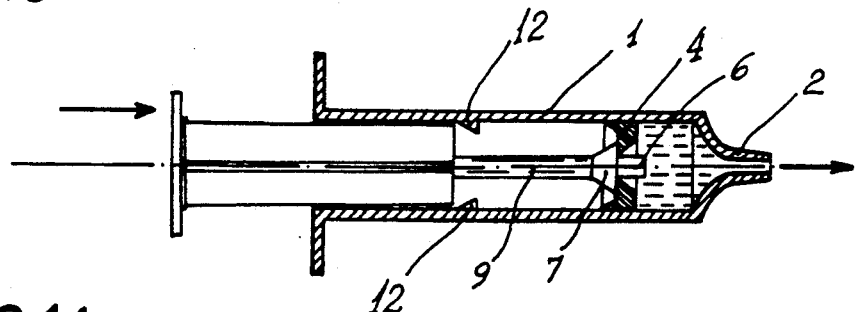
Figure 12:
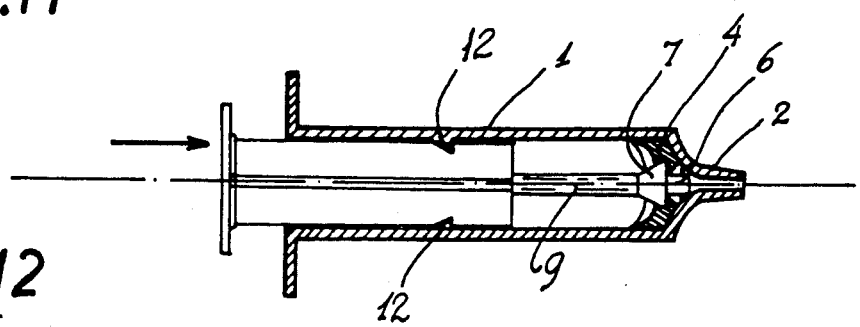

From the position shown in FIG. 10 it is possible to put pressure on the stem, as the group of the elements 4 and 7 act like a piston, and the medium introduced into the syringe can be ejected through the spout 2 as shown in FIG. 11 up to the end of the displacement shown in FIG. 12.

If the suction is again desired the piston cannot operate, since the element 7 will be separated from the element 4 because they will not be physically joined to each other. This is clearly shown in FIG. 12. Therefore, the syringe cannot be used again.

If one intends to place the element 7 in the position of FIG. 8, this would be impossible. The reason is that the guide-butt 6 will prevent it since it would have be touching the bottom of the syringe which will not allow the element 4 to pass through the hole 5.

It will be understood that each of the elements described above, or two or more together, may also find a useful application in other types of constructions differing from the types described above.

While the invention has been illustrated and described as embodied in a self-discarding syringe, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A self-discarding syringe, comprising a tube having a spout at an end thereof; and piston means including two elements movable relative to each other and including a first element which is rigid and a second element which is resilient, one of said two elements being an exterior element, while another of said two elements being an interior element, said interior element having a butt projecting at a spout side of said interior element and a stem projecting at an opposite side of said interior element, so that before use of the syringe said interior element and said butt are located at a spout side of said one element, then for use of the syringe said interior element is pulled through said exterior element to an opposite side of said one element, then said interior element displaces said exterior element toward said spout to expel a content of the syringe from said tube through said spout, and at an end of the displacement said butt abuts against said spout so that said interior element cannot be again moved through said exterior element to its spout side and therefore said exterior element cannot be moved by said interior element away from said spout for a reuse of the syringe.

2. A self-discarding syringe as set forth in claim 1, wherein said exterior element has an external contour corresponding to an internal contour of said tube, and a hole in its center.

3. A self-discarding syringe as set forth in claim 2, said interior element has a shape selected from the group consisting of a truncated conical shape, a cylindrical shape, a semicylindrical shape and a polygonal shape.

4. A self-discarding syringe as set forth in claim 2, wherein said interior element has a cylindrical shape.

5. A self-discarding syringe as set forth in claim 2, wherein said interior element has a polygonal shape.

6. A self-discarding syringe as set forth in claim 1, and further comprising limitation means for limiting displacement of said piston means away from said spout, said limitation means including bosses formed on an inner surface of said tube and angularly spaced by 120°.

7. A self-discarding syringe as set forth in claim 6, wherein said bosses are formed by rectangular flattening of said tube.

8. A self-discarding syringe as set forth in claim 6, wherein said bosses are formed by making depressions in said tube.

9. A self-discarding syringe as set forth in claim 1, wherein said limitation means includes projections formed on an inner surface of said tube and angularly spaced by 120°.

* * * * *